(12) United States Patent
DuBuffet et al.

(10) Patent No.: US 7,208,607 B1
(45) Date of Patent: Apr. 24, 2007

(54) PROCESS FOR SYNTHESIS OF PERINDOPRIL AND PHARMACEUTICALLY ACCEPTABLE SALTS THEREOF

(75) Inventors: Thierry DuBuffet, Autretot (FR); Pascal Langlois, Saint Jean de la Neuville (FR)

(73) Assignee: Les Laboratoires Servier, Courbevoie Cedex (FR)

( * ) Notice: Subject to any disclaimer, the term of this patent is extended or adjusted under 35 U.S.C. 154(b) by 0 days.

(21) Appl. No.: 10/580,148

(22) PCT Filed: Nov. 18, 2004

(86) PCT No.: PCT/FR2004/002936

§ 371 (c)(1),
(2), (4) Date: May 18, 2006

(87) PCT Pub. No.: WO2005/054276

PCT Pub. Date: Jun. 16, 2005

(30) Foreign Application Priority Data

Nov. 19, 2003 (EP) ................... 03292864

(51) Int. Cl.
C07D 209/12 (2006.01)
A61K 31/403 (2006.01)
(52) U.S. Cl. .................... 548/452; 514/412
(58) Field of Classification Search ........... 548/452; 514/412
See application file for complete search history.

(56) References Cited

FOREIGN PATENT DOCUMENTS

EP 0308341 3/1998

OTHER PUBLICATIONS

Seble Wagaw, et al, "Palladium-catalyzed coupling of optically active amines with aryl bromides" Journal of the American Chemical Society, vol. 119, No. 36, pp. 8451-8458, 1997.
International Search Report for PCT/FR2004/002936 issued May 13, 2005.
EPO Search Report for EP03 292864.0 issued Mar. 23, 3004.
International Preliminary Examination Report for PCT/FR2004/002936 of Jun. 6, 2006.

*Primary Examiner*—Kamal A. Saeed
*Assistant Examiner*—Michael P. Barker
(74) *Attorney, Agent, or Firm*—Hueschen and Sage

(57) ABSTRACT

Process for the synthesis of perindopril of formula (I):

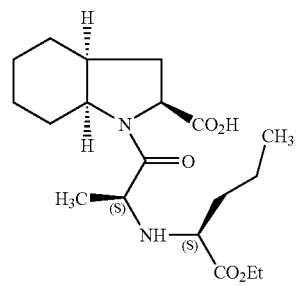

and pharmaceutically acceptable salts thereof.

12 Claims, No Drawings

PROCESS FOR SYNTHESIS OF PERINDOPRIL AND PHARMACEUTICALLY ACCEPTABLE SALTS THEREOF

The present invention relates to a process for the synthesis of perindopril of formula (I):

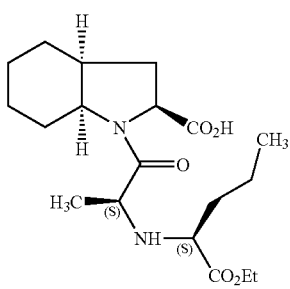

(I)

and pharmaceutically acceptable salts thereof.

Perindopril and its pharmaceutically acceptable salts, and more especially its tert-butylamine salt, have valuable pharmacological properties.

Their principal property is that of inhibiting angiotensin I converting enzyme (or kininase II), which allows, on the one hand, prevention of the conversion of the decapeptide angiotensin I to the octapeptide angiotensin II (a vasoconstrictor) and, on the other hand, prevention of the degradation of bradykinin (a vasodilator) to an inactive peptide.

Those two actions contribute to the beneficial effects of perindopril in cardiovascular diseases, more especially in arterial hypertension and heart failure.

Perindopril, its preparation and its use in therapeutics have been described in European patent specification EP 0 049 658.

In view of the pharmaceutical value of this compound, it has been important to be able to obtain it by an effective synthesis process, readily transposable to an industrial scale, that leads to perindopril in a good yield and with excellent purity starting from reasonably priced starting materials.

Patent specification EP 0 308 341 describes the industrial synthesis of perindopril by the coupling of (2S,3aS,7aS)-octahydroindole-2-carboxylic acid benzyl ester with N-[(S)-1-carboxybutyl]-(S)-alanine ethyl ester, followed by deprotection of the carboxylic group of the heterocycle by catalytic hydrogenation.

The Applicant has now developed a new process for the synthesis of perindopril that uses readily obtainable starting materials.

More specifically, the present invention relates to a process for the synthesis of perindopril and pharmaceutically acceptable salts thereof, which process is characterised in that the compound of formula (II), of configuration (S):

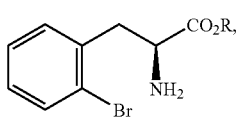

(II)

wherein R represents a hydrogen atom or a protecting group for the acid function, is reacted with a compound of formula (III), of configuration (R):

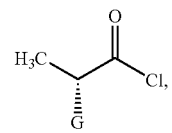

(III)

wherein G represents a chlorine or bromine atom or a hydroxy, p-toluenesulphonyloxy, methanesulphonyloxy or trifluoromethanesulphonyloxy group, in the presence of a base to yield the compound of formula (IV):

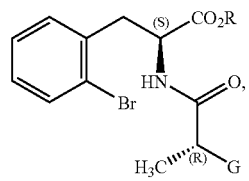

(IV)

wherein R and G are as defined hereinbefore, which is subjected to an intramolecular coupling reaction to yield the compound of formula (V):

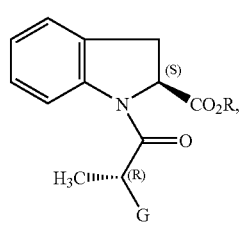

(V)

wherein R and G are as defined hereinbefore, which is reacted with the compound of formula (VI):

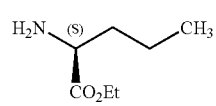

(VI)

to yield the compound of formula (VII):

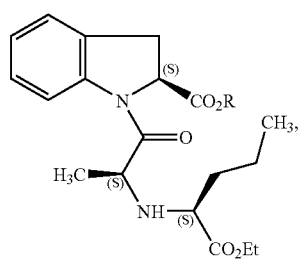

(VII)

wherein R is as defined hereinbefore, which is subjected to a catalytic hydrogenation reaction to yield, after deprotection where appropriate, the compound of formula (I).

Among the protecting groups for the acid function there may be mentioned, without implying any limitation, the groups benzyl and linear or branched $(C_1-C_6)$alkyl.

Among the bases that can be used for the reaction between the compounds of formula (II) and (III) there may be mentioned, without implying any limitation, organic amines, such as triethylamine, pyridine or diisopropylethylamine, and mineral bases, such as NaOH, KOH, $Na_2CO_3$, $K_2CO_3$, $NaHCO_3$ or $KHCO_3$.

The intramolecular coupling reaction is preferably carried out either in the presence of a base and a catalyst based on palladium or using sodium hydride and copper(I) iodide or copper(I) bromide.

The catalysts based on palladium which are preferably used in the coupling reaction are catalysts based on palladium and on an arylphosphine or bisphosphine.

Among those catalysts there may be mentioned, without implying any limitation, Pd(0)/PPh$_3$, Pd(0)/P(o-tolyl)$_3$, Pd(0)/P(1-naphthyl)$_3$, Pd(0)/P(o-methoxyphenyl)$_3$, Pd$_2$(dba)$_3$/PPh$_3$, Pd$_2$(dba)$_3$/P(o-tolyl)$_3$, Pd$_2$(dba)$_3$/P(1-naphthyl)$_3$, Pd$_2$(dba)$_3$/P(o-methoxyphenyl)$_3$, Pd$_2$(dba)$_3$/P(2-furyl)$_3$, Pd$_2$(dba)$_3$/dppp, Pd$_2$(dba)$_3$/(±)-BINAP and (DPPF)PdCl$_2$.CH$_2$Cl$_2$/DPPF, BINAP being understood to be 2,2'-bis(diphenylphosphino)-1,1'-binaphthyl, dba being understood to be dibenzylideneacetone, DPPF being understood to be 1,1'-bis(diphenylphosphino)ferrocene and dppp being understood to be 1,3-bis(diphenylphosphino)propane.

Among the bases that can be used for the coupling reaction in the presence of a catalyst based on palladium there may be mentioned, without implying any limitation, $Cs_2CO_3$, NaOtBu, $Na_2CO_3$, NaOAc and KOAc.

When G represents a chlorine or bromine atom or a p-toluenesulphonyloxy, methanesulphonyloxy or trifluoromethanesulphonyloxy group, the reaction between the compounds of formulae (V) and (VI) is preferably carried out in the presence of a base, preferably an organic amine, such as triethylamine, pyridine or diisopropylethylamine, or a mineral base, such as $Na_2CO_3$, $K_2CO_3$, $NaHCO_3$ or $KHCO_3$.

When G represents a hydroxy group, the reaction between the compounds of formulae (V) and (VI) is preferably carried out in the presence of an activation reagent, such as N-methyl-N-phenyl-aminotriphenylphosphonium iodide, or, when R is other than a hydrogen atom, by a Mitsunobu reaction.

The compounds of formula (IV) are new products which are useful as synthesis intermediates in the chemical or pharmaceutical industry, especially in the synthesis of perindopril, and as such form an integral part of the present invention.

The compounds of formula (II) can be prepared according to the procedure described in the publication *J. Am. Chem. Soc.* 1994, 116, 10847–10848.

EXAMPLE 1
(2S, 3aS, 7aS)-1-{(2S)-2-[(1S)-1-(Ethoxycarbonyl)-butylamino]-propionyl}-octahydro-1H-indole-2-carboxylic acid tert-butylamine salt Step A: Benzyl (2S)-3-(2-bromophenyl)-2-{[(2R)-2-bromopropanoyl]amino}-propanoate Introduce 25.7 g of benzyl (S)-2-bromophenylalaninate and 150 ml of dichloromethane into a reactor, then bring the temperature of the reaction mixture to 0° C. and add 20 ml of diisopropylethylamine followed by 13.2 g of (2R)-2-bromopropionyl chloride. Subsequently, bring the mixture to ambient temperature. After stirring for 1 hour at that temperature, wash the mixture with water and then with dilute acetic acid solution, and evaporate off the solvents to yield the title compound.

Step B: Benzyl (2S)-1-[(2R)-2-bromopropanoyl]-2-indolinecarboxylate

Introduce 15.5 g of the compound obtained in the Step above, dissolved in toluene, 1.57 g of Pd$_2$(dba)$_3$, 1.83 g of P(o-tolyl)$_3$ and 21.5 g of Cs$_2$CO$_3$ into a reactor. Then bring the reaction mixture to 100° C. After stirring for 15 hours at that temperature, the mixture is brought back to ambient temperature and purified by chromatography over silica to yield the title compound.

Step C: Benzyl (2S)-1-((2S)-2-{[(1S)-1-(ethoxycarbonyl)butyl]amino}-propanoyl)-2-indolinecarboxylate Introduce 12.3 g of ethyl (2S)-2-aminopentanoate, 16 ml of triethylamine and 16 ml of acetonitrile into a reactor; then bring the mixture to 60° C., slowly add a solution of 19.4 g of the compound obtained in the Step above, dissolved in dichloromethane, and reflux for 4 hours. After returning to ambient temperature, wash the mixture with water and with dilute acetic acid solution; then evaporate off the solvents to yield the title compound.

Step D: (2S, 3aS, 7aS)-1-{(2S)-2-[(1S)-1-(Ethoxycarbonyl)-butylamino]-propionyl}-octahydro-1H-indole-2-carboxylic acid Introduce 20 g of the compound obtained in the Step above, dissolved in acetic acid, and then 0.5 g of 10% Pd/C into a hydrogenator. Hydrogenate under a pressure of 0.5 bar between 15 and 30° C., until the theoretical amount of hydrogen has been absorbed. Remove the catalyst by filtration and then cool to between 0 and 5° C. and collect the resulting solid by filtration. Wash the cake and dry it to constant weight to yield the title compound with an enantiomeric purity of 99%.

Step E: (2S, 3aS, 7aS)-1-{(2S)-2-[(1S)-1-(Ethoxycarbonyl)-butylamino]-propionyl}-octahydro-1H-indole-2-carboxylic acid tert-butylamine salt The precipitate obtained in the Step above (20 g) is dissolved in 280 ml of ethyl acetate, and then 4 g of tert-butylamine and 40 ml of ethyl acetate are added.

The resulting suspension is then refluxed until dissolution is complete; then the resulting solution is filtered whilst hot and cooled to a temperature of 15–20° C., with stirring. The precipitate obtained is then filtered off, made into a paste again using ethyl acetate, dried and then ground to yield the expected product in a yield of 95%.

EXAMPLE 2

(2S, 3aS, 7aS)-1-{(2S)-2-[(1S)-1-(Ethoxycarbonyl)-butylamino]-propionyl}-octahydro-1H-indole-2-carboxylic acid tert-butylamine salt Step A: (2S)-3-(2-Bromophenyl)-2-{([(2R)-2-bromopropanoyl]amino}-propanoic acid Introduce 28.8 g of (S)-2-bromophenylalanine, 7.5 ml of water and 15 ml of toluene into a reactor; then bring the mixture to between 0 and 5° C. and add 25 ml of 5M sodium hydroxide solution and then a solution of 20.2 g of (2R)-2-bromopropionyl chloride in toluene, whilst keeping the temperature below 10° C. and maintaining the pH of the mixture at 10 by adding 5M sodium hydroxide solution. After stirring for a further 1 hour at 10° C., add concentrated hydrochloric acid to bring the pH of the mixture to 6.

Separate off the toluene phase and then add concentrated hydrochloric acid to the aqueous phase to bring the pH to 2.

The precipitate formed is then filtered off and dried to yield the title compound.

Step B: Identical to Step B of Example 1

Step C: (2S)-1-((2S)-2-{[(1S)-1-(Ethoxycarbonyl)-butyl]-amino}-propanoyl)-2-indolinecarboxylic acid Introduce 10.5 g of ethyl (2S)-2-aminopentanoate, 13.5 ml of triethylamine and 13.5 ml of acetonitrile into a reactor; then bring the mixture to 60° C. and slowly add a solution of 19.3 g of the compound obtained in the Step above in 130 ml of dichloromethane, and then reflux for 4 hours. After returning to ambient temperature, wash the mixture with water and with dilute acetic acid solution; then evaporate off the solvents to yield the title compound.

Steps D and E: Identical to Steps D and E of Example 1

EXAMPLE 3

(2S, 3aS, 7aS)-1-{(2S)-2-[(1S)-1-(Ethoxycarbonyl)-butylamino]-propionyl}-octahydro-1H-indole-2-carboxylic acid tert-butylamine salt Step A: Benzyl (2S)-3-(2-bromophenyl)-2-{[(2R)-2-(p-toluenesulphonyloxy)-propanoyl]-amino}-propanoate Introduce 25.7 g of benzyl (R)-2-bromophenylalaninate and 150 ml of dichloromethane into a reactor; then bring the temperature of the reaction mixture to 0° C. and add 20 ml of diisopropylethylamine and then 20.2 g of (1R)-2-chloro-1-methyl-2-oxoethyl-p-toluenesulphonate chloride. Then bring the mixture to ambient temperature. After stirring for 1 hour at that temperature, wash the mixture with water. The solvents are then evaporated off to yield the title compound.

Steps B to E: Identical to Steps B to E of Example 1

The invention claimed is:

1. A process for the synthesis of a compound of formula (I):

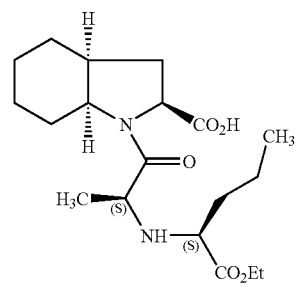

and pharmaceutically acceptable salts thereof,
wherein a compound of formula (II), of configuration (S):

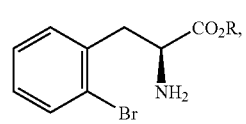

wherein R represents a hydrogen atom or a protecting group,
is reacted with a compound of formula (III), of configuration (R):

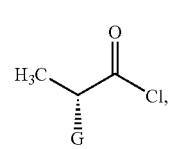

wherein G represents chlorine, bromine, hydroxy, p-toluenesulphonyloxy, methanesulphonyloxy or trifluoromethanesulphonyloxy,
in the presence of a base
to yield a compound of formula (IV):

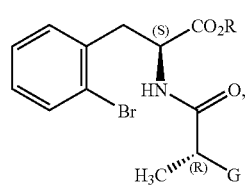

which is subjected to an intramolecular coupling reaction to yield a compound of formula (V):

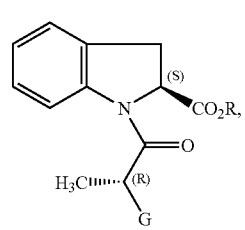

which is reacted with a compound of formula (VI):

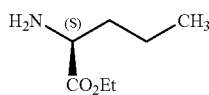

to yield a compound of formula (VII):

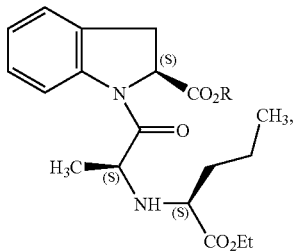

which is subjected to a catalytic hydrogenation reaction to yield, after deprotection where appropriate, the compound of formula (I).

2. The process of claim 1, wherein R represents a benzyl or linear or branched ($C_1$–$C_6$)alkyl group.

3. The process of claim 1, wherein the intramolecular coupling reaction is carried out either in the presence of a base and a catalyst based on palladium or using sodium hydride and copper(I) iodide or copper(I) bromide.

4. The process of claim 3, wherein the intramolecular coupling reaction is carried out in the presence of a base and a catalyst based on palladium and an arylphosphine or bisphosphine.

5. The process of claim 4, wherein the base used for the intramolecular coupling reaction is selected from $Cs_2CO_3$, NaOtBu, $Na_2CO_3$, NaOAc and KOAc.

6. The process of claim 4, wherein the catalyst based on palladium and an arylphosphine or bisphosphine is selected from Pd(0)/$PPh_3$, Pd(0)/P(o-tolyl)$_3$, Pd(0)/P(1-naphthyl)$_3$, Pd(0)/P(o-methoxyphenyl)$_3$, $Pd_2$(dba)$_3$/$PPh_3$, $Pd_2$(dba)$_3$/P(o-tolyl)$_3$, $Pd_2$(dba)$_3$/P(1-naphthyl)$_3$, $Pd_2$(dba)$_3$/P(o-methoxyphenyl)$_3$, $Pd_2$(dba)$_3$/P(2-furyl)$_3$, $Pd_2$(dba)$_3$/dppp, $Pd_2$(dba)$_3$/(±)-BINAP and (DPPF)PdCl$_2$.$CH_2Cl_2$/DPPF, it being understood that:

BINAP means 2,2'-bis(diphenylphosphino)-1,1'-binaphthyl,
dba means dibenzylideneacetone,
DPPF means 1,1'-bis(diphenylphosphino)ferrocene
and dppp means 1,3-bis(diphenylphosphino)propane.

7. The process of claim 1, wherein G represents chlorine, bromine, p-toluenesulphonyloxy, methanesulphonyloxy or trifluoromethanesulphonyloxy.

8. The process of claim 7, wherein the reaction between the compounds of formulae (V) and (VI) is carried out in the presence of an organic amine selected from triethylamine, pyridine and diisopropylethylamine or a mineral base selected from $Na_2CO_3$, $K_2CO_3$, $NaHCO_3$ and $KHCO_3$.

9. The process of claim 1, wherein G represents hydroxy.

10. The process of claim 9, wherein the reaction between the compounds of formulae (V) and (VI) is carried out in the presence of N-methyl-N-phenyl-aminotriphenylphosphonium iodide or, when R is other than a hydrogen atom, under Mitsunobu reaction conditions.

11. A compound of formula (IV):

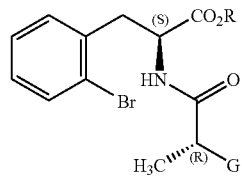

wherein R represents a hydrogen atom or a protecting group, and G represents chlorine, bromine, hydroxy, p-toluenesulphonyloxy, methanesulphonyloxy or trifluoromethanesulphonyloxy.

12. A process according to claim 1 for the synthesis of perindopril in the form of its tert-butylamine salt.

* * * * *